United States Patent [19]

Iovine et al.

[11] Patent Number: 4,803,071

[45] Date of Patent: Feb. 7, 1989

[54] HAIR CARE COMPOSITIONS

[75] Inventors: Carmine P. Iovine, Bridgewater; Frank A. Nowak, Jr., Somerville, both of N.J.

[73] Assignee: National Starch and Chemical Corporation, Bridgewater, N.J.

[21] Appl. No.: 617,416

[22] Filed: Jun. 5, 1984

Related U.S. Application Data

[63] Continuation of Ser. No. 120,185, Feb. 11, 1980, abandoned.

[51] Int. Cl.$^4$ .................. A61K 7/06; A61K 7/08; A61K 7/11; A61K 9/12
[52] U.S. Cl. ................. 424/70; 424/DIG. 1; 424/DIG. 2; 424/DIG. 4; 424/47
[58] Field of Search ................. 424/70, 47

[56] References Cited

U.S. PATENT DOCUMENTS

| | | | |
|---|---|---|---|
| 3,715,428 | 2/1973 | Quasius et al. | 424/DIG. 2 X |
| 3,986,825 | 10/1976 | Sokol, I | 424/DIG. 2 X |
| 3,996,146 | 12/1976 | Tarasov et al. | 424/DIG. 2 X |
| 4,027,008 | 5/1977 | Sokol, II | 424/DIG. 2 X |
| 4,035,478 | 7/1977 | Mullen | 424/DIG. 2 X |
| 4,048,301 | 9/1977 | Papantonion | 424/DIG. 2 X |
| 4,131,576 | 12/1978 | Iovine et al. | 260/17.4 GC |

FOREIGN PATENT DOCUMENTS 847267  10/1976  Belgium ..................... 424/70

Primary Examiner—Dale R. Ore
Attorney, Agent, or Firm—Ellen T. Dec; Edwin M. Szala

[57] ABSTRACT

Hair care formulations are prepared which comprise a carrier and a functional amount of a cationic water soluble graft copolymer of a N,N-dialkyldiallyl ammonium halide on a substrate of cellulose, galactomannon gum or derivative thereof, wherein the graft copolymers are characterized by a nitrogen content within the range of 0.25 to 4.5%, and are prepared by a unique polymerization process.

6 Claims, No Drawings

HAIR CARE COMPOSITIONS

This application is a continuation of application Ser. No. 120,185, filed Feb. 11, 1980 now abandoned.

BACKGROUND OF THE INVENTION

I. Field of the Invention

This invention relates to improved hair care compositions containing a specified cationic water soluble graft copolymer of N,N-dialkyldiallyl ammonium halide on a substrate of cellulose, galactomannon gum or derivative thereof.

II. Brief Description of the Prior Art

One of the more widely used methods of conditioning human hair is by the application of cationic materials which are absorbed by the protein structure of the hair. Especially useful in this application have been the cationic fatty quaternary compounds having chain lengths in their fatty substituents of about 8 to 18 carbon atoms. These, however, are relatively low molecular weight, oily, waxy materials which can make the hair feel greasy, excessively soften the hair and leave it limp, unmanageable and without body, particularly after repeated useage. In order to overcome such problems, certain water soluble cationic polymers which provide the positive features of the low molecular weight quaternary fatty compounds while also imparting a degree of body and hair set (hold) have been proposed. Thus, U.S. Pat. No. 4,035,478, for example, teaches the use of a high molecular weight copolymer of vinyl pyrrolidone and quaternized dimethylaminoethyl methacrylate in a clear, hair conditioning composition while U.S. Pat. No. 3,816,616 teaches the use of o-alkyltrimethylammonium chloride substituted anhydroglucose polymers in unitary shampoos and cream rinses.

Homopolymers and copolymers of N,N-dialkyldiallyl ammonium chloride have been recognized in the hair care field for their ability to provide certain desirable properties to hair when formulated into shampoos, cream rinses, hair fixatives and other compositions. Thus, U.S. Pat. Nos. 3,986,825, 3,996,146 and 4,027,008, among others, teach the use of such polymers in hair care applications. Use of hair care products formulated with such polymers does, however, leave the hair with an undesirable, greasy feel and relatively poor holding properties and consequently, to date, no product containing these polymers has been successful commercially.

Further, Belgian Pat. No. 847,267 teaches the use in hair care products of various copolymers prepared by the reaction of unsaturated monomers including N,N-diallyl-N,N-dialkyl ammonium halides, with a range of hydroxyl containing polymers in a very dilute aqueous medium in the presence of ceric ions. Although the patent teaches that in some instances, depending on the substrates employed, graft copolymers may be produced, repeated attempts to prepare specific copolymers of N,N-dialkyldiallyl ammonium chloride and cellulose or galactomannon gum using the method of the Belgian patent have resulted in the production of either a highly crosslinked, water insoluble copolymer or a copolymer of such low graft efficiency (and consequent low nitrogen substitution) as to be commercially impractical. Additionally, when the latter graft copolymer was formulated into a hair care product, it displayed poor hair holding power, particularly under humid conditions. Moreover, the use of ceric salts in cosmetic formulations may be undesirable due to the toxicological problems generally associated with the presence of residual amounts of transition metals.

It is therefore an object of the present invention to provide hair care compositions which facilitate manageability of the hair, contribute to the desirable improved appearance or feel and/or hold the hair in place without the greasiness or reduced hold power achieved using the presently available polymers and copolymers.

It is a further object of the invention to provide hair care compositions containing cationic water soluble graft copolymers of a N,N-dialkyldiallyl ammonium halide on substrates of cellulose, galactomannon gum or derivatives thereof.

SUMMARY OF THE INVENTION

These and related objects are accomplished with hair care formulations, preferably conditioning shampoos, hair fixatives and hair rinses comprising an appropriate carrier together with a functional amount of a cationic water soluble graft copolymer of a N,N-dialkyldiallyl ammonium halide and a substrate selected from the group consisting of cellulose, galactomannon gums and derivatives thereof, said graft copolymers being characterized by a nitrogen content within the range of about 0.25 to 4.5%. Such graft copolymers are prepared by suspending the cellulose or galactomannon gum in an organic polymerization solvent and adding thereto an aqueous solution of the N,N-dialkyldiallyl ammonium halide. Graft polymerization of the resultant two-phase mixture is carried out in the presence of a free radical polymerization catalyst with agitation at a temperature of from about 40° to 100° C., wherein it is required that at least one of the phases i.e., the suspended cellulose or gum or the aqueous solution of N,N-dialkyldiallyl ammonium halide monomer, contain a suitable surfactant. It is important that the organic solvent used in the cellulose or gum phase be immiscible with the aqueous monomer solution phase, that it not dissolve the monomer or graft copolymer as it is formed and that it have a boiling point at or above the temperature of the polymerization reaction.

The improved hair care compositions of the present invention are prepared by formulating the specific graft copolymer in an appropriate carrier together with other functional and/or optional ingredients as known in the art for the particular end uses desired. The resultant hair care compositions are characterized by good combability, gloss, adhesion to hair, resistance to static generation and superior holding properties even under conditions of high humidity.

DETAILED DESCRIPTION OF THE PREFERRED EMBODIMENTS

As already described above the graft copolymers used herein comprise N,N-dialkyldiallyl ammonium halides on substrates of cellulose, galactomannon gum or derivatives thereof. The N,N-dialkyldiallyl ammonium halide monomers suitable in preparing the graft copolymers are those containing 1-6 carbon atoms in the alkyl group, with N,N-dimethyl diallyl ammonium chloride being preferred. Representative galactomannon gums useful as substrates include guar gum and locust bean gum. Also useful as substrates herein are cellulose, and its derivatives such as the hydroxyethyl, hydroxypropyl, methyl, ethyl and carboxymethyl derivatives as well as the corresponding derivatives of the galactomannon gums. Mixtures of the above monomers or substrates may also be used in preparing the graft copolymers. It will be recognized by those skilled in the art that there may also be optionally present at least one copolymerizable comonomer. In order to be useful herein, the comonomers must have a minimum solubility of 5% by weight in water at 25° C., must be unsaturated and capable of polymerizing by free radical initiation. Suitable comonomers include acrylic and methacrylic acid, acrylamide, methacrylamide, mono- or di-N-substituted acrylamides and methacrylamide, vinyl pyrrolidone, sodium or ammonium styrene sulfonate, hydroxyalkyl acrylates and methacrylates, etc. Thus, for convenience, our use of the term N,N-dialkyldiallyl ammonium halide monomer shall be understood to designate any mixture of comonomers wherein up to about 25% by weight of the N,N-dialkyldiallyl ammonium halide monomer may be replaced by any of the above described comonomers. In order to obtain the desired properties of the resultant hair care compositions, it is essential that the graft copolymer used herein be water soluble (or readily dispersible) and have a nitrogen content within the range of about 0.25 to 4.5%.

The specific graft copolymers may be used as the functional component in virtually any hair care composition when formulated with the appropriate carriers. Although conditioning shampoos, hair fixatives and hair rinses represent the preferred end uses, the graft copolymers may also be used as conditioning agents in permanent waving lotions, hair straighteners, or hair dyes; as fixing agents in hair dyes to facilitate dye pickup and in other topical applications. In general, such conditioning/fixative compositions comprise aqueous or aqueous-alcoholic solutions of the graft copolymer in concentrations of about 0.1 to 10%, preferable 0.5 to 2.5% by weight of the total composition together with other necessary and/or optional functional ingredients. Suitable alcohols for use in these formulations include ethanol, isopropanol, n-propanol, etc.

More specifically, shampoo formulations, in addition to the carrier and graft copolymer which is preferably used in an amount of 0.1-2.0% by weight, there is also present one or more anionic, cationic nonionic or amphoteric surfactants (detergents) as commonly known in the art. Particularly desirable shampoo formulations will include both amphoteric and anionic surfactants.

Examples of suitable amphoteric surfacts are the alkali metal salts of long chain alkyl ($C_8$-$C_{18}$) imidazoline derivatives having either one or two carboxylic acid groups substituted on the nitrogen atom in the 1 position of the imidazolidyl ring; the higher alkyl and higher alkyl amino alkyl substituted betaines wherein said higher alkyl groups contain from 8-18 carbon atoms; the long chain ($C_8$-$C_{18}$) amino sulfonates; the sulfonated alkyl amines, wherein said alkyl groups contain from 8-18 carbon atoms, and the N-alkyl-beta-amino propionic acids, wherein the alkyl group contains 8-18 carbon atoms.

Exemplary nonionic surfactants include the polyoxyalkylene alkyl ethers and the condensates of alkylene oxides with fatty acids. Suitable long chain amine oxides which are nonionic in basic solution and cationic in acid solution include dimethyl lauryl amine oxide, dimethyl cetyl amine oxide, dimethyl stearyl amine oxide, etc.; and the long chain cyclic amine oxide such as lauryl morpholine oxide and the like.

Exemplary anionic surfactants include the higher fatty alcohol sulfates such as, for example, sodium lauryl sulfate; the alkylaryl sulfonates, e.g. sodium or potassium isopropylbenzene sulfonates, isopropyl naphthalene sulfonates; the alkali metal higher alkyl sulfosuccinates, e.g. sodium octenyl sulfosuccinate, sodium N-methyl-N-palmitoyl taurate, sodium oleyl isothionate; the alkali metal salts of alkylarylpolyethoxyethanol sulfates or sulfonates, e.g. the sodium t-octylphenoxypolyethoxyethyl sulfates and sulfonates having from 1 to 5 oxyethylene units.

Aside from the various types of anionic, synthetic detergents mentioned above, the lauryl sulfoacetamide type, sulfated fatty acyl monoethanolamide, sodium stearate, and the sodium salts of the long chain ($C_8$-$C_{18}$) acyl-sarcosinates made by condensing a fatty acid chloride with N-methyl glycine, are also useful in the practice of this invention.

Exemplary cationic surfactants include the cetyltrimethyl ammonium salts and the corresponding coconut fatty and octadecyl analogues, the higher alkyl dimethylmethallylammonium halides wherein said alkyl groups have from 8 to 18 carbon atoms, e.g., octyl, decyl, dodecyl, or octadecyl, t-octylphenoxyethoxydimethylbenzylammonium chloride, the dialkylguanidines and biguanidines, wherein the alkyl groups contain from 8-20 carbon atoms, cetyl dimethyl amine acetate, lauryl piperidinium chloride, the 2-alkyl-tetrahydroindoles, etc.

The total surfactant level generally employed in these conditioning shampoo formulations is within the range of 5 to 25% solids by weight of the total formulation. Optional components in such shampoos include dyes, fragrance, preservative, bactericides, protein, lanolin and its derivatives, foam boosters, etc.

When the graft copolymers are used with the carrier in preparing hair fixative or rinse formulations they are preferably present in amounts of 0.1 to 2.0%. The optional components present therein include perfumes, opacifiers, combing aids, protein, aerosol propellents, thickeners, gelling agents, etc.

PREPARATION OF THE GRAFT COPOLYMER

It is apparent that suitable graft copolymers for use herein must be prepared by a unique polymerization process in order to achieve such characteristics as are required in the hair care products of the present invention. This process polymerization that the reaction be carried out at high solids concentration to produce copolymers at high grafting efficiency, generally in excess of 75% and high conversion. This unique polymerization process is described in co-pending U.S. Pat. No. 4,131,576 issued Dec. 26, 1978 to C. P. Iovine et al.

In accordance therewith, the cellulose or gum is suspended in an organic solvent thereby forming a continuous phase which, optionally, may contain a solvent-soluble-surfactant (discussed hereinbelow) in an amount of 1-12% by weight of the solvent. The solvent chosen must be one which is immiscible with water, which does not dissolve the cellulose, gum, N,N-dialkyldiallyl ammonium halide monomer or the graft copolymer as it is formed, and which has a boiling point at or above the temperature at which the graft polymerization reaction will be carried out. Suitable solvents are selected from aromatic and aliphatic hydrocarbons as well as certain chlorinated hydrocarbons and include benzene, dichlorobenzene, toluene, xylene, 1,2-dichloroethane, heptane, octane, isooctane and nonane as well as other solvents within the described parameters known to those skilled in the art. Mixtures of such solvents may also be used.

The catalyst chosen must be of the type wherein the initiator species is generated in the aqueous phase of the reaction mixture in which the substrate and monomer are present. Suitable catalyst systems useful herein are those such as hydrogen peroxide/ferrous salt; inorganic alkali metal or ammonium persulfates; organic hydroperoxides, etc. They may be used alone or in the form of redox pairs, i.e., in admixture with compounds having a reducing effect, for example, alkali metal bisulfates or sodium formaldehyde sulfoxylate. The use of ceric based catalysts are not included within the scope of the invention for reasons presented hereinabove. The preferred catalysts are the ammonium or potassium persulfate salts. The concentration of catalyst employed may range from 0.1 to 2% based on the weight of the cellulose or gum component of the graft. The catalyst may be added directly to the aqueous monomer solution or added to the entire reaction mixture as a separate catalyst solution. Alternatively, if the catalyst is a redox pair consisting of water soluble component and a solvent soluble component, such components are added to the respective reaction phases. The desired grafting may also be initiated by irradiation of the reaction mixture.

In general, any type of surfactant, i.e. nonionic, anionic or cationic, may be employed in the preparation of the graft copolymers useful in the hair care products of the present invention with the anionic and nonionic surfactants being preferred. Particularly suitable surfactants are the oil-soluble polyhydroxyethylated compounds known as nonionic surfactants for example, hydroxyethylated nonyl phenols, hydroxyethylated long chain monocarboxylic acids and fatty acids, fatty acid esters of sorbitol and hydroxyethylated fatty acid esters of sorbitol. The usually applied cationically active and anionically active emulsifiers, such as the alkyl aryl sulfonates, linear alkyl sulfonates and sulfates, for example, lauryl sulfate or sulfosuccinic acid ester, may also be used, if desired, instead of or in admixture with substances of the nonionic type. The suitability of a specific surfactant for its use in the present invention may be easily ascertained by preparing an aliquot of the intended mixture to determine if a stable suspension is formed. Specifically, however, the choice of the particular surfactant (or surfactants) to be employed will depend on a number of factors including the nature of the continuous phase, the ratio of substrate to monomer, the specific dialkyl monomer and substrate used, the concentration of monomer in the aqueous phase; and the pH conditions under which the polymerization reaction occurs. If a water-soluble surfactant is employed, it is incorporated into the aqueous phase and used in amounts of 0.5 to 12% based on the weight of the substrate. When a solvent-soluble surfactant is employed, it is incorporated into the homogeneous phase at levels of 1–12% based on the weight of the solvent. When both types of surfactants are employed, they are added to the respective phases generally within the same levels disclosed hereinabove.

Other additives conventionally used by those skilled in the art in the graft polymerization reaction will generally be added to the aqueous monomer solution.

The concentration of monomer substrate, buffer(s) and catalyst in the aqueous phase is designed to be in the range of 50–90% and preferably 60–80% solids, by weight, by varying the amount of water used to prepare the solution. The concentration of "polymer" (i.e. substrate and monomer) in the continuous phase is designed at 15–50% solids, by weight, by adjusting the amount of organic solvent. The reaction mixture is deoxygenated and heated to the appropriate temperature (within about 40° to 100° C.) to initiate polymerization. Polymerization is continued at this elevated temperature with stirring until the desired degree of conversion and grafting has been achieved (usually after ½ to 6 hours, depending upon the method of initiation). At the end of this period, the beads are filtered off from the continuous phase, (washed with an inert solvent, if desired) and dried.

EXAMPLE 1

This example illustrates the preparation of a graft copolymer of dimethyldiallyl ammonium chloride and hydroxyethyl cellulose suitable for use in the hair care products of the present invention.

A reactor assembly consisting of a 12 liter flask, a Freidrich condenser, thermometer and agitator was charged with 5250 parts Isopar E (mixed $C_{10}$ avg. isoparaffin available from Exxon Corp.) and 157.5 parts sorbitan monooleate. With agitation, 1658 parts of a 2.5 M.S. hydroxyethyl cellulose (2% solution 4000–6000 cps; moisture content 5%) was sifted into the reactor over 15 minutes.

To the above suspension, at 25° C., 846.7 parts of an aqueous solution of N,N-dimethyldiallylammonium chloride at 62% activity was slowly added from a dropping funnel over 45 minutes. When the monomer addition was complete, a solution consisting of: 107.8 parts water, 0.53 parts tetrasodiumethylenediamine tetra acetic acid, 27.3 parts disodium hydrogen phosphate and 9.45 parts ammonium persulfate was slowly added to the suspension, from a dropping funnel over a 15 minute period.

The reaction mixture at this point consisted of small uniform spheres containing the cellulose derivative, monomer, catalyst, buffer and water. The concentration of water in the spheres was about 20 wt.%.

The reaction mixture was alternatively evacuated to 20 mm Hg and repressurized to 0.5 psi with nitrogen gas several times. After the last degassing cycle, the reaction was maintained at 0.5 psi with nitrogen and heat was applied to a temperature of 65°–70° C. with a 30 minute heat-up period. The batch was maintained at 65°–70° C. for 4 hours during which time graft polymerization occurred and the small uniform beads remained intact.

After the required heating time the batch was cooled to 25° C. and centrifuged at 2000 RPM. The centrifuge cake was washed with 4000 parts of 95% isopropanol and discharged on to perforated trays. The product was dried in a forced draft oven at 40° C. until the volatiles content was 92–97%. The final product (2475 parts) consisted of offwhite, uniform, free flowing beads (95% pass through 20 mesh) having the following analysis:

Volatiles Content, 6.5%
2% sol. Viscosity (25° C., 20 RPM) 190 cps.
% Nitrogen (dry basis), 2.05%
Residual Monomer, 1.5%
I.V. (1N KCl), 3.2 dl/gm

EXAMPLES 2–9

Using the technique outlined above, graft copolymers were prepared using the ingredients shown in Table I:

TABLE I

| Ingredient | Example No. | | | | | | | |
|---|---|---|---|---|---|---|---|---|
| | 2 | 3 | 4 | 5 | 6 | 7 | 8 | 9 |
| Polymer A* (95% non-volatiles) | 39.5 | 26.3 | — | — | — | — | — | — |
| Polymer B* (95% non-volatiles) | — | — | — | 237 | — | — | — | — |
| Polymer C* (95% non-volatiles) | — | — | 39.5 | — | — | — | — | — |
| Polymer D* (95% non-volatiles) | — | — | — | — | 79 | 73.7 | 79 | 105 |
| Isopar E | 125 | 125 | 125 | 750 | 250 | 250 | 250 | 300 |
| Sorbitan monooleate (HLB 4.5) | 6.3 | 6.3 | 6.3 | 22.5 | 7.5 | 7.5 | 7.5 | 15 |
| Sodium dodecyl benzene sulfonate | — | — | 1.2 | — | — | — | — | — |
| Dimethyl diallylammonium chloride (60% aqueous) | 21 | 42 | 21 | 125 | 33.3 | 33.3 | 40 | 167 |
| Methacrylamide | — | — | — | — | 5.0 | 11.0 | — | — |
| Sodium acrylate | — | — | — | — | — | — | 1.5 | — |
| Water | 11.0 | 8.0 | 12.0 | 11 | 9.3 | 10 | 10.5 | — |
| Tetrasodium EDTA | 0.04 | 0.04 | 0.04 | 0.075 | 0.02 | 0.020 | 0.025 | 0.05 |
| Ammonium persulfate | 0.25 | 0.19 | 0.23 | 1.35 | 0.45 | 0.45 | 0.45 | 0.60 |
| Disodium hydrogen phosphate | 0.69 | 0.20 | 0.69 | 3.9 | 1.3 | 1.3 | 1.3 | 1.30 |
| % Volatiles | 8 | 6.5 | 5 | 11 | 8.5 | 6 | 5.6 | 13 |
| % Nitrogen (d.b., dialyzed) | 0.5 | 2.9 | 1.8 | 2.13 | 2.48 | 3.30 | 1.80 | 4.1 |
| IV (1N KCl) | 4.85 | 5.50 | 3.8 | 7.5 | 3.0 | 2.8 | 4.0 | 1.2 |

*Polymer A: 3.0 M.S. Hydroxypropylcellulose 1% soln 1500–2500 cps
Polymer B: 2.5 M.S. Hydroxyethylcellulose 1% soln 1500–2500 cps
Polymer C: 1.8 M.S. Hydroxyethylcellulose 2% soln 4500–6500 cps
Polymer D: 2.5 M.S. Hydroxyethylcellulose 3% soln 4500–6500 cps

EXAMPLE 10

This example illustrates the preparation of a graft copolymer of dimethyldiallyl ammonium chloride and guar gum suitable for use in the hair care products of the present invention.

A two liter multi-neck flask equipped with an all glass agitator, thermometer and condenser was charged with 250 parts Isopar E and 7.5 parts Sorbitan monooleate. To this solution 79 parts of a medium viscosity guar gum (1% viscosity 4000 cps) was added with agitation. A fluid suspension resulted to which was slowly added, from a dropping funnel over a 15 minute period at 25° C., 41 parts of a 61% aqueous solution of dimethyldiallyl ammonium chloride monomer.

An aqueous solution consisting of: 7.2 parts water, 0.025 parts Na₄EDTA, 1.3 parts Na₂HPO₄, and 0.45 parts (NH₄)₂S₂O₈ was prepared and also slowly added to the suspension over a 15 minute period. The reaction mixture which consisted of small uniform spheres suspended in the solvent, was degassed as described in Example No. 1. The mixture was heated and stirred at 65°–70° C. for 5 hours. After the heating period, the batch was cooled and filtered on a Buchner suction apparatus. The wet cake was resuspended in 400 ml isopropanol, refluxed for 4 hours, cooled and refiltered. Drying was accomplished at 40° C. under forced draft for 4 hours. The final product consisted of small uniform spheres which passed 100% through a 20 mesh screen.

A 1% solution of the resulting polymer was prepared in water and exhibited a viscosity of 715 cps. The solid polymer had a volatiles content of 5%, a Nitrogen content of 2.8% (d.b.) and an I.V. of 5.4 in 1N KCl.

EXAMPLE 11

In a manner similar to Example No. 10, a graft copolymer was prepared from locust bean gum of medium viscosity using the following ingredients:

| | Parts |
|---|---|
| Isopar E | 125 |
| Sorbitan monooleate | 6.3 |
| Locust Bean Gum at 95% | 39.5 |
| Sodium dodecyl benzene sulfonate | 1.3 |
| Dimethyldiallylammonium chloride at 60% | 21 |
| Tetrasodium EDTA | 0.040 |
| Water | 12 |
| Na₂HPO₄ | 0.69 |
| (NH₄)₂S₂O₈ | 0.23 |

The solid polymer had a volatiles content of 9% and a nitrogen content of 2.75% (d.b.)

The graft copolymers prepared in Examples 1–11 were then used in formulating hair care products in the following examples.

EXAMPLE 12

The copolymers prepared in Examples 1, 4, 5, 6, 7, 8, and 9 were each used to form clear hair rinse compositions. Thus, hair rinse compositions were prepared by mixing two grams of each of the dry copolymers with 98 grams distilled water, respectively, at room temperature until completely dissolved. The resultant compositions were then tested using the following procedure.

One cc. of the test composition was evenly distributed in each of a series of eight test swatches of virgin brown European hair which had been previously shampooed and rinsed. The swatches were 10" in length and weighed approximately 2 grams each. After the composition had been evenly distributed through the swatches, they were rinsed thoroughly with warm water. Excess water was squeezed out by pulling the swatch between the thumb and index finger. The hair was found to be more manageable, was easier to comb and had more body than control swatches which had not been treated with the hair rinse composition.

Similarly, opaque cream rinses were prepared as above but using graft copolymers from Examples 2, 3, 10 and 11. These rinses also gave superior properties, comparable to those observed above.

EXAMPLE 13

A conditioning shampoo was prepared using the graft copolymer of Example 1 by dissolving the copolymer in water and thereafter adding the remaining ingredients in the order and amounts shown:

| | |
|---|---|
| Copolymer of Example 1 | 0.30 |
| Distilled water | 47.45 |
| Cocoamido betaine[1] | 15.00 |
| TEA lauryl sulfate[2] | 35.00 |
| Tetrasodium EDTA | 0.25 |
| Lauric diethanolamide[3] | 2.00 |
| Dye, perfume, preservative | Q.S. |

[1]Varion CADG (32% active) - Ashland Chemical Company
[2]Maprofix TL5-500 (40% active) - Onyx Chemical Company
[3]Monamid 716 (100% active) - Mona Industries After dissolution, the composition was adjusted to pH 5-7 with citric acid.

The resultant composition was then tested as follows:

Ten-inch long/2 gram swatches of virgin brown European hair were wetted with warm water. Five drops of the test shampoo were applied to the hair and lathered by massaging between the fingers. The hair was then rinsed under warm tap water for about 15 seconds after which lathering and rinsing were repeated and excess water removed by blotting. The hair was left in a conditioned state. It had excellent wet combing; and dried soft, silky, and glossy. There was no sign of undesirable copolymer buildup on repeated use.

The shampoo was also evaluated by an 8 person test panel for a one week period. Participants found excellent lather and cleansing, ease of combability, and added body. Similar shampoo compositions were prepared using the graft copolymers of Examples 2, 4, 5, 6, 7, 9 and 10. On testing, comparable results were obtained.

EXAMPLE 14

A hair fixative was prepared using the graft copolymer of Example 1 by mixing 2 grams of the copolymer with 98 grams water and agitating until solution was complete.

One cc. of the hair fixative was applied to each of eight test swatches of virgin brown European hair which had been previously shampooed and rinsed. Swatches were each 10 inches in length and weighed approximately 2 grams. The composition was evenly distributed throughout the swatches and combed through. The composition imparted excellent wet combing and desnarling. The treated hair swatches were then curled on a ½ inch diameter teflon mandril and allowed to dry. The mandril was removed and the hair uncoiled into a helix configuration. The dry, treated, curled hair swatches were placed in a chamber at 70° F. and 90% relative humidity. The curls showed excellent resistance to the effects of high humidity.

Subsequently, the swatches were found to be easily combed when dry, had good gloss and body, and static resistance. The polymer was easily removed from the hair with conventional shampoos.

EXAMPLE 15

A series of aerosol propelled hair fixatives were prepared using the graft copolymer of Example 1 and the ingredients shown below. In all cases, the polymer was dissolved in water, the ethanol slowly added with agitation and then the additives. The resulting solutions were poured into aerosol cans, the vapor space evacuated, valves crimped and charged with propellant.

| | Formulation | | | | |
|---|---|---|---|---|---|
| | 1 | 2 | 3 | 4 | 5 |
| Graft Polymer | 0.50 | 0.50 | 0.50 | 0.50 | 0.50 |
| Distilled Water | 74.50 | 64.50 | 54.50 | 44.50 | 34.50 |
| Anhydrous Ethanol | x | 10.00 | 20.00 | 30.00 | 40.00 |
| Additives | QS. | QS. | QS. | QS. | QS. |
| Propellant A-46 (blend of isobutane and propane) | 25.00 | 25.00 | 25.00 | 25.00 | 25.00 |

All formulations provided superior properties to the hair when used. Formulations 1 and 2 were used as aerosol "foaming lotions" while Formulations 3, 4 and 5 (with higher ethanol levels) were non-foaming in use.

EXAMPLE 16

For comparison purposes, similar hair care compositions were prepared using polymerized dimethyldiallyl ammonium chloride (av. M.W. less than 100,000) and compared with one prepared using the graft copolymer of Example 1.

Test solutions were prepared using 2% polymer and 2% of the graft copolymer, respectively, 15% ethanol and 83% water. Curl retention of treated swatches of hair placed in chamber at 70° F. and 90% relative humidity was noted at various intervals as indicated below.

| | % Curl Retention* | |
|---|---|---|
| Time Interval | Graft Copolymer | Poly(dimethyldiallyl ammonium chloride) |
| 30 minutes | 62.1% | 31.9% |
| 60 minutes | 46.6% | 23.4% |
| 90 minutes | 44.4% | 23.0% |
| 120 minutes | 42.4% | 22.5% |

*mean of 12 swatches per sample.

Films of the test solutions were thereafter evaluated by casting 2% solutions of the polymer and the graft copolymer, respectively, in the form of 6 mil films on glass air dried, then equiliberated at 70° F./90% RH for 1 hour. Both films were equally clear, however, the poly(dimethyldiallyl ammonium chloride) was sticky (tacky) while the film of the graft copolymer remained non-sticky.

The degree of stickiness was also tested by dipping swatches of hair in the test solutions, drying at 120° F. for 1 hour and equilibrating at 70° F./90% RH for up to 3 hours. At each hourly interval the hair treated with the polymerized dimethyldiallyl ammonium chloride was sticky while that treated with the composition of the invention remained nonsticky. In this same comparison test, the hair treated with the polymerized dimethyldiallyl ammonium chloride was observed to be totally limp without noticeable stiffness or body while that treated with the composition of the present invention become somewhat stiffened and more full-bodied.

Comparison tests were also made using clear hair rinse compositions prepared with polymerized dimethyldiallyl ammonium chloride and those prepared using hair rinses prepared with graft copolymers in accordance with the present invention. In these tests a series of 10 inch, 2 gram hair swatches were wetted with water. Excess water was squeezed out. One half of the swatches were each treated with 6 drops of a 2% solution and the other half similarly treated with the graft copolymer of Example 1. Lotions were massaged into the hair for 10 seconds then rinsed out under warm tap water for an additional 10 seconds. Excess water was squeezed out. Wet combing of the pairs of swatches (8 sets) was evaluated by a panel of 8 persons who found combability easier with the graft copolymer of polymerized dimethyldiallyl ammonium chloride.

EXAMPLE 17

For comparison purposes, dimethyldiallyl ammonium chloride and hydroxyethyl cellulose were copolymerized in the presence of ceric ions using the procedure disclosed in Belgian Pat. No. 847,267.

A 3 liter, 4 neck flask equipped with an agitator, thermometer and condenser was charged with 1000 parts distilled water and 52.6 parts 2.5 M.S. hydroxyethyl cellulose (95% non-volatiles) of medium molecular weight. The polymer/water mixture was stirred 3 hours at 25° C. to insure complete solution. To this mixture was added, 27.2 parts of a 62.5% solution of N,N-dimethyldiallyl ammonium chloride monomer. The reaction mixture was vacuum deoxygenated by repeated evacuations to 1 mm Hg and repressurization to 0.5 psi with nitrogen. After warming to 30°-35° C., 25 ml of 0.1N $Ce^{+4}$ (1N $HNO_3$) catalyst solution was added. The mixture was stirred at 30°-35° C. for 24 hours to insure polymerization. The batch was cooled to 25° C. and the product was precipitated by the addition of acetone. The precipitate was collected by filtration and dried at 40° C. forced air.

Analysis of the resultant product showed a nitrogen content of only 0.15% (d.b.) and a % conversion of 6.8%. This copolymer was designated as the control. The resultant copolymers were used in the formulation of a variety of hair care products and tested for curl retention in the manner shown in Example 16 and the results are as follows:

| Time Interval | % Curl Retention* | |
|---|---|---|
| | Graft Copolymer | Control |
| 30 minutes | 64.9% | 52.4% |
| 60 minutes | 52.2% | 42.3% |
| 90 minutes | 48.6% | 39.2% |
| 120 minutes | 46.9% | 37.9% |

*mean of 12 swatches per sample tested at 70° F./90% RH.

When tested for conditioning properties, the formulations containing the graft copolymers of Example 1 were more moisture resisting and harder holding thereby imprating greater stiffness, body and adhesion to the hair during brushing and combing.

EXAMPLES 18-19

These examples illustrate the preparation and use of additional graft copolymers in which a minor portion of the N,N-dialkyldiallyl ammonium halide component is replaced by a copolymerizable comonomer. Thus, graft copolymers were prepared using the procedure of Example I and the following ingredients.

| Ingredient | Examples | |
|---|---|---|
| | 18 | 19 |
| Hydroxyethylcellulose (Polymer B) | 237 | 79 |
| Isopar E | 750 | 250 |
| Sorbitan Monooleate | 11.5 | 7.5 |
| N,N—dimethyldiallylammonium chloride (60%) | 100 | 39 |
| Methacrylamide | 15 | — |
| Acrylic Acid at pH 8.3 | — | 1.0 |
| Water | 22 | 7.5 |
| Tetrasodium EDTA | 0.06 | 0.025 |
| Ammonium Persulfate | 1.35 | 0.45 |
| Disodium Hydrogen Phosphate | 3.9 | 1.3 |
| % Volatiles | 6.4 | 5.6 |
| % Nitrogen | 2.48 | 1.9 |
| IV (IN KCl) | 3.0 | 4.01 |

When the resultant copolymers were used in conditioning shampoos and hair fixatives as described in Examples 12-15, similar superior results were observed.

EXAMPLE 20

Graft copolymers may be prepared using the general procedure described in Example 1 but varying the monomer employed. Thus, graft copolymers prepared, for example, with N,N-dimethyldiallyl ammonium bromide, N,N-diethyldiallyl ammonium chloride and N-ethyl-N-butyl diallyl ammonium chloride may be employed in the hair fixative/conditioning products of the present invention with results comparable to those observed above.

Variations may be made in proportions, procedures and materials without departing from the scope of the invention as defined by the following claims.

We claim:

1. An improved hair conditioning composition selected from the group consisting of rinses, lotions, shampoos, and fixatives, comprising an aqueous or aqueous alcoholic carrier and a polymer of N,N-dialkyldiallyl ammonium bromide or chloride, wherein the improvement comprises improved manageability provided by the presence in the composition of from 0.30 to 2% by weight of a water-soluble cationic graft copolymer prepared by polymerizing about 21-25% by weight of a N,N-dialkyldiallyl ammonium halide monomer with about 75-79% by weight of a substrate selected from the group consisting of hydroxyethyl cellulose and hydroxypropyl cellulose the polymerization being carried out in a two-phase system in the presence of a free radical polymerization catalyst other than ceric ions which comprises the steps of:
   (a) suspending the substrate in an organic solvent, which solvent has a boiling point at or above the temperature of the polymerization reaction, is immiscible with water and does not dissolve the substrate, monomer or graft copolymer;
   (b) adding thereto an aqueous solution of the monomer thereby forming a suspension of discrete aqueous spheres in the organic solvent phase;
   (c) deoxygenating and heating the reaction mixture in the presence of the free radical polymerization catalyst to a temperature of 40°-100° C. to initiate polymerization;
   (d) continuing the polymerization for from 0.5-6 hours; and
   (e) isolating the resultant graft copolymer from the reaction mixture in the form of solid beads; wherein it is required that either the aqueous solution or the substrate suspension or both contain a cationic, anionic or nonionic surfactant and that the solids content of the aqueous polymerization mixture is greater than 50% by weight.

2. The improved hair conditioning composition of claim 1, wherein from 0.33 to 1% by weight of the water-soluble cationic graft copolymer prepared by polymerizing about 25% by weight of N,N-dimethyldiallyl ammonium chloride monomer with about 75% by weight of hydroxyethyl cellulose substrate is present.

3. The improved hair conditioning composition of claim 2, wherein the conditioning composition is the lotion and wherein the graft copolymer is present in an amount of about 0.2%

4. The improved hair conditioning composition of claim 2, wherein the conditioning composition is the rinse and wherein the graft copolymer is present in an amount of about 0.2%.

5. The improved hair conditioning composition of claim 2, wherein the conditioning composition is the shampoo and wherein the graft copolymer is present in an amount of about 0.33%.

6. The improved hair conditioning composition of claim 1, wherein about 25% by weight of at least one surfactant is present.

* * * * *